United States Patent
Kim

(10) Patent No.: US 7,078,065 B2
(45) Date of Patent: *Jul. 18, 2006

(54) COMPOSITION CONTAINING ASIASARI RADIX EXTRACTS FOR PROTECTING BRAIN CELLS AND IMPROVING MEMORY

(76) Inventor: Sung-Jin Kim, Chungryangri-Dong 60. Hanshin APT 104-2003., Dongdaemoon-Ku Seoul 130-010 (KR)

( * ) Notice: Subject to any disclaimer, the term of this patent is extended or adjusted under 35 U.S.C. 154(b) by 0 days.

This patent is subject to a terminal disclaimer.

(21) Appl. No.: 10/814,495

(22) Filed: Mar. 31, 2004

(65) Prior Publication Data
US 2004/0247716 A1   Dec. 9, 2004

Related U.S. Application Data

(63) Continuation of application No. 10/080,052, filed on Feb. 21, 2002, now Pat. No. 6,737,087.

(30) Foreign Application Priority Data

Mar. 13, 2001  (KR) ................ 2001-12840
Aug. 22, 2001  (KR) ............ 2001-0050670

(51) Int. Cl.
*A61K 35/78*  (2006.01)

(52) U.S. Cl. ............ 424/773; 424/725; 424/451; 424/464; 424/489

(58) Field of Classification Search ........... 424/773, 424/725, 451, 464, 489
See application file for complete search history.

(56) References Cited

U.S. PATENT DOCUMENTS 5,889,046 A   3/1999  Akimoto et al.
6,737,087 B1  5/2004  Kim

FOREIGN PATENT DOCUMENTS

KR   2001-0007646 A   *  2/2001

* cited by examiner

*Primary Examiner*—Susan D. Coe
(74) *Attorney, Agent, or Firm*—Stetina Brunda Garred & Brucker

(57) ABSTRACT

The present invention discloses that fractions of Asiasari Radix extract have the ability to induce neuroprotection against AMPA (-amino-3-hydroxy-5-methyl-4-isoxazole propionic acid)-induced damages in brain cells as well as stimulation of memory.

14 Claims, 15 Drawing Sheets

IP : anti-IR Ab
Blot : anti-pTyr Ab

← β subunit

← IgG

Cont　Fr. 2　Fr. 1　Fr. 4

COMPOSITION CONTAINING ASIASARI RADIX EXTRACTS FOR PROTECTING BRAIN CELLS AND IMPROVING MEMORY

This in a continuation of application Ser. No. 10/080,052, filed Feb. 21, 2002, now U.S. Pat. No. 6,737,087.

BACKGROUND OF THE INVENTION

This invention is related to a composition for protecting brain cells and improving memory comprising Asiasari Radix extracts.

One of the major factors involved in brain cell damages is glutamate. Glutamate exerts its actions by binding to four types of receptors including NMDA receptor, AMPA receptor, Kainate receptor and 1S,3R-ACPD receptor (Craig CR, Stitzel RE, Modern Pharmacology with clinical applications, 293–302, 1997). When brain ischemia occurs, oxygen supply to brain cells diminishes and then anaerobic glycolysis increases. Therefore, ATP content in the cell decreases and the concentration of extracellular potassium ions increases. Eventually, depolarization of neuronal cell membrane and subsequent release of excitatory amino acids occurs which results in the neuronal damages by the activation of receptors for NMDA, AMPA and Kainate. Excitotoxicity via excitatory neurotransmitters induces cellular stress and thereby plays an important role in the pathogenesis of neurodegenerative disorders such as Alzheimer's disease, Parkinson disease, strokes and amyotrophic lateral sclerosis [Haloween, B., J. Neurochem. 59, 1609–1623, 1992; Coyle, J. T. and Puttfarcken, P., Science 262, 689–695. 1993; Olanow, C. W., Trends. Neurosci. 16, 439–444, 1993].

Neurodegenerative disorders in the central nervous system are often accompanied by a decrease in cognition and memory. Especially, dementia is a serious problem of modern societies with high population of elderly. Dementia is typically caused by a variety of environmental factors such as genetics, aging, brain damage, smoking and alcohol and other complex factors. The hippocampus of patients suffering from dementia is heavily damaged and this is closely related to the reduction of acetylcholine levels in the brain.

Acetylcholinesterase inhibitors are clinically used for the Alzheimer's disease to increase acetylcholine levels. Recently, a great number of researches have been performed to search for ways of neuroprotection such as by using NMDA antagonist, AMPA antagonist, GABA agonist, intracellular calcium decreasing agent, nitric oxide inhibitor, free radical scavenger, Na channel blocker, inhibitor of glutamate release, acidosis, hypothermia and potassium channel activator [Gagliardi RJ, Neuroprotection, excitatotoxicity and NMDA antagonists, Arq. Neuro-Psiquiatr. 58, 2000].

Dozocyilpin (MK 801), selfotel, cerestat, and dextrometorfan have been developed as NMDA antagonists. However, they are known to induce altered sensory perception, dysphoria, nystagmus, and hypotension at low doses, while inducing psychological adverse events such as excitement, paranoia, and hallucination at higher doses. Furthermore, NBQX was developed as an AMPA antagonist. However, it causes severe kidney toxicity and is thus not optimal in clinical applications. Therefore, neuroprotective agents without toxicity from natural product-derived materials need to be developed.

Recently, it has been found that AMPA receptor plays an important role in the development of Alzheimer's disease. The fact that neuronal cell damages by the AMPA receptor activation occurs selectively at the basal forebrain cholinergic neurons (BFCNs) suggests that development of anti-Alzheimer's disease can be tried by using AMPA receptor antagonists [Weiss, J. H., et al., Basal forebrain cholinergic neurons are selectively vulnerable to AMPA/kainate receptor-mediated neurotoxicity. Neuroscience 60, 659–664, 1994].

Glial cells are essential for the survival of neuronal cells. In developing the central nervous system, glial cells control the precise movement and growth of neuronal cells whereas they play a role in homeostasis and synaptic plasticity of neuronal cells after development. In addition, glial cells contain receptors and neurotransmitters capable of initiating neuronal signal transduction essential for survival and apoptosis of neuronal cells. Thus, protecting glial cells from external damages are eventually related to the plasticity, homeostasis and survival of neuronal cells.

Insulin receptor in the peripheral tissues participates mainly in the glucose metabolism whereas its role in the CNS appeared not to be related to glucose metabolism but other neuronal activity such as memory. In fact, insulin receptor is widely distributed in different areas in the brain and present in a large amount in the hippocampus. Hence, the hippocampus is an important target of insulin action in the brain. Recently, much evidence has been presented as to the role of brain insulin or insulin receptors in the memory formation. It has been found that both experimental damage to the neuronal insulin receptor and Alzheimer brain induced similar metabolic abnormalities [Hoyer, S., Muller, D, Plaschke, K. Desensitization of brain insulin receptor. Effect on glucose/energy and related metabolism. J. Neural Transm [Suppl] 44, 259–268, 1994].

Interesting hypothesis has been proposed that sporadic Alzheimer disease might be the brain type of non-insulin dependent diabetes mellitus (Hoyer, S. Is sporadic Alzheimer disease the brain type of non-insulin dependent diabetes mellitus? A challenging hypothesis. J. Neural Transm. 105, 415–422, 1998). It has been suggested that intracerebroventricular insulin enhances memory in a passive-avoidance task [Park, C. P., Seeley, R. J., Craft, S. and Woods S. C. (2000) Intracerebroventricular insulin enhances memory in a passive avoidance task. Physiol. Behav. 68, 509–514]. Insulin receptor density and tyrosine kinase activity in the sporadic Alzheimer's disease (SAD) or sporadic dementia of Alzheimer's type (SDAT) were known to be significantly decreased [Frolich, L., Blum-degen, D., Bernstein, H. G., Engelsberger, S., Humrich, J., Laufer, S., Muschner, D., Thalheimer, A., Turk, A., Hoyer, S., Zochling, R., Boissl, K. W., Jellinger, K., and Piederer, P. Brain insulin and insulin receptors in aging and sporadic Alzheimer's disease. J. Neural Transm. 105, 423–438, 1998]. Interestingly, tyrosine phosphorylation of the hippocampal insulin receptor has been shown to play an essential role in spatial memory formation [Zhao, W., Chen, H., Xu, H., Moore, E., Meiri, N., Quon, M. J., Alkon, D. L. (1999) Brain insulin receptors and spatial memory. J. Biol. Chem. 274, 34893–34902, 1999].

BRIEF SUMMARY OF THE INVENTION

Recently, it has been found that ERK (Extracellular signal-Regulated Kinase or MAPK) I and II, which are important downstream signaling mediators of the insulin receptor, are implicated in memory and learning [Thiels, E, Klann, E. Extracellular signal-regulated kinase, synaptic plasticity, and memory. Rev. Neurosci. 12, 327–345, 2001; Sweat J. D. The neuronal MAP kinase cascade: a biochemical signal integration system subserving synaptic plasticity and memore. J. Neurochem. 76, 1–10 2001]. It has been also demonstrated that rats subjected to avoidance learning showed significant and specific increases in the activated forms of ERK I and II in the rat hippocampus [Cammarota, M., Bevilaqua, L. R. M. Ardenghi, P. Paratcha G., de Stein, M. L., Iaqueirdo I., Medina, J. H. Learning-associated activation of nuclear MAPK, CREB and Elk-1, along with Fos production, in the rat hoppocampus after a one-trial avoidance learning; abolition by NMDA receptor blockade. Mol. Brain Res. 76 36–46, 2000]. Taken together, insulin receptor and ERK I/II activators could be used for memory enhancement in addition to cholinesterase inhibitors.

BRIEF DESCRIPTION OF THE DRAWINGS

These as well as other features of the present invention will become more apparent upon reference to the drawings wherein.

DETAILED DESCRIPTION OF THE INVENTION

Figure 1:
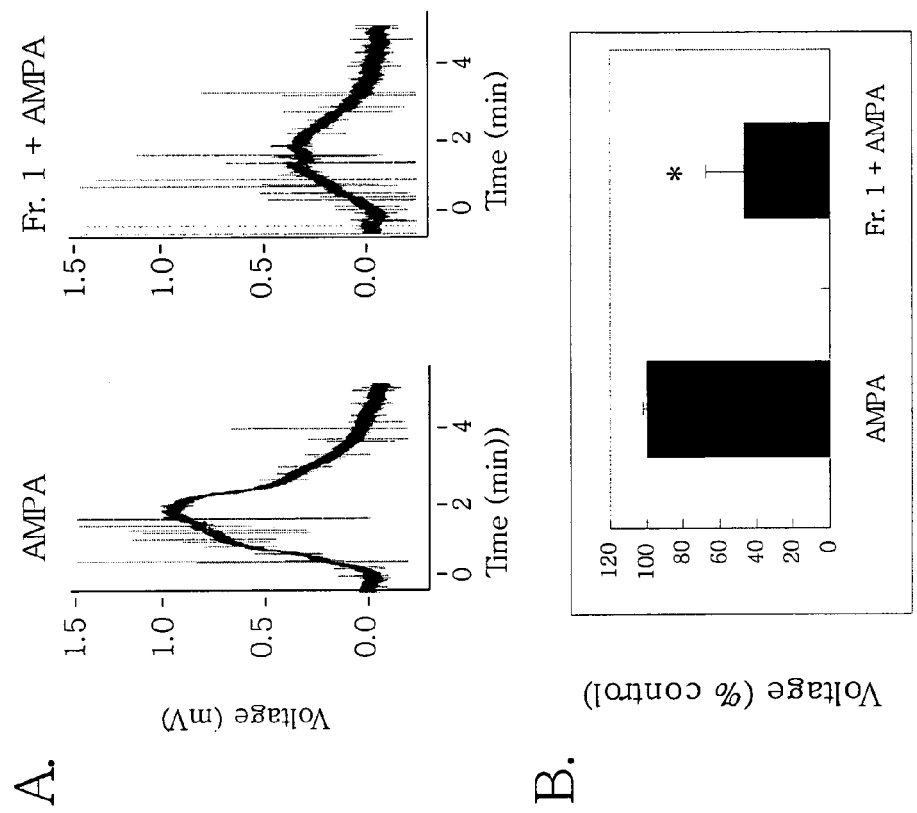
FIG. 1 shows fraction 1 of Asiasari Radix (AR) extract blocking the depolarization induced by AMPA in the rat cortical slices. Data are expressed as mean SD (n=5). *: p 0.05 with respect to the control.

The inventor of the present invention has studied for many years to search for neuroprotective agents with memory enhancing activity for the moderns who are being subjected to brain damages due to environmental factors such as various stress, alcohol, smoking etc. Based on the search of many natural products, it was found that Asiasari Radix extracts have significant neuroprotective effects as well as memory enhancing activity.

In this respect, the present invention is related to a composition containing Asiasari Radix extracts for protecting brain cells and improving memory. A feature of the composition of the present invention is that it contains 0.5 to 50% by weight of Asiasari radix extracts per total weight of the composition.

Asiasari Radix is the dried wholeplant, rhizome or root of *Asarum sieboldi* F. MAEKAWA, *Asarum sieboldi* var. seoulense Nakai, *Asarum sieboldii* Miq., Asarum heterotropoides Schmidt, *Asarum heterotropoides* var. *mandshuricum* Kitagawa, or *Asiasarum heterotropoides* F. MAEKAWA var. *seoulensis* F. MAEKAWA. It is a perennial plant. Its rhizome projecting aside is relatively short and it contains a lot of knobs and fine roots with a diameter of approximately 1 mm. It is shaped like an uneven and crooked string. It has a knotty rhizome with a diameter of 3–5 mm and is yellowish brown. The rhizome contains a lot of roots with 5–20 cm in length. It has a light brown color and is long and slender. It has very shallow vertical pleats.

It contains essential oils such as methyleugenol, asarylketone, cineol, safrole, limonen, eucarvone and acidamide such as N-isobutyl 2, 4, 8, 10-dodecatetraenamide, pellitorin and lignans such as sesamin and asarinin (Zhou RH, Resource Science of Chinese Medicinal Materials. pp. 202–211. Beijing: China medical & Pharmaceutical Sciences press, 1993). Several alkaloids including hygenamine are also present in Asiasari Radix. Extracts of Asiasari Radix have been reported to exert body temperature decreasing, spasmolytic, antihistamine and cardiotonic actions. It is used as local anesthetics, fever remedy, cough remedy, expectorant and diuresis. (Zhu, Y. Chinese Materia Medica: Chemistry, Pharmacology and Application, pp. 66–69. Beijing: People's Health Publisher, 1998). However, it is not known as to whether Asiasari Radix extract has any effects on neuroprotection and memory.

Asiasari Radix extracts of the present invention are obtained by extracting Asiasari Radix with a lower alcohol having 1 carbon atom to 4 carbon atoms such as methanol or ethanol, and organic solvent such as acetone, chloroform, methylenechloride, ether or ethylacetate at 5° C. to 80° C., desirably 30° C. to 55° C. for 15 min to 48 hrs, desirably 30 min to 12 hrs. The obtained extracts can be made as powders by evaporation under reduced pressure.

In addition, the Asiasari Radix extracts of the present invention could be further fractionated by the following method (Harborne J. B. Phytochemical methods: A guide to modern techniques of plant analysis. 3rd Edt. Pp 6–7, 1998).

The Asiasari Radix extracts of the present invention are prepared by the following sequential extraction and fractionation procedure: the extracts of Asiasari Radix obtained by the above mentioned method are dissolved in a methanol: water mixed solvent, adjusted to pH 2–4 and followed by extraction with equal volume of chloroform; the chloroform-insoluble fraction is adjusted to pH 9–12 with NH4OH and subjected to extraction with equal volume of a chloroform: methanol mixed solvent; among these, a fraction insoluble in the chloform:methanol mixed solvent is subsequently subjected to extraction with methanol to obtain the Asiasari Radix extracts.

Desirable ratios of chloroform:methanol mixture solvent are in the ranges of 1: 0.1~1. When the chloroform-insoluble fractions described above are further fractionated with chloroform:methanol, the fraction soluble in the chloroform: methanol mixed solvent contains most alkaloids while the fraction insoluble in the chloroform:methanol mixture solvent contains quaternary alkaloids and N-oxides.

The composition comprising Asiasari Radix extracts could contain suitable carriers, excipients and diluents such as lactose, dextrose, sucrose, sorbitol, mannitol, xylitol, erythritol, maltitol, starch, acacia gum, alginate, gelatin, calcium, phosphate, calcium silicate, cellulose, methyl cellulose, microcrystalline cellulose, polyvinyl pyrollidone, water, methylhydroxy-benzoate, propylhydroxybenzoate, talc, magnesium stearate or mineral oil. The composition according to the present invention can be used as oral formulations such as powders, tablets, capsules, suspensions, emulsions, syrups, aerosol and external application and suppositories. In addition, it could be used as sterilized injections. The Asiasari Radix extracts in the present invention can be administered at the dosage of 0.1 mg/Kg to 500 mg/Kg per day. The dosage can be administered once or it can be administered as divided. However, the actual dose administered should be understood in terms of various related factors such as kind of diseases to treat, administration route, age of patient, gender and weight, and the condition of disease, etc. Therefore, above-mentioned dosage does not limit the range of the present invention by any ways. The composition comprising Asiasari Radix extracts in the present invention can be widely used as drugs, foods and drinks for neuroprotection and memory improvement. Asisari Radix extracts can be added to foods such as various foods, drinks, gum, tea, vitamin complexes and health foods etc.

In addition, the present invention is related to a composition for improving memory containing a chloroform fraction of Asiasari Radix extracts obtained by the following sequential fractionation procedure: Asiasari Radix is subjected to extraction with a lower alcohol having between 1 carbon atom and 4 carbon atoms such as methanol or ethanol, or organic solvent such as acetone, chloroform, methylene chloride, ether or ethylacetate; the resulting Asiasari Radix extracts are solubilized in a methanol:water mixed solvent, adjusted to pH 2–4 with acid and subjected to extraction with equal volume of chloroform to obtain the chloroform fraction of Asiasari Radix extracts. Desirable ratios of the methanol:water mixed solvent are in the ranges of 1: 0.2~1.5 and this fraction contains terpenoids and phenolic compounds.

The composition for improving memory of the present invention has a feature that the content of the fraction described above ranges 0.5 to 50% by weight per total weight of the composition.

The composition for improving memory of the present invention could contain suitable carriers, excipients and diluents as same as the composition containing Asiasari Radix extracts for protecting brain cells and improving memory as described above. In addition, it could be made as various formulations according to conventional methods and be widely used as drugs, foods, and drinks for improving memory.

The present invention is explained in detail by the following examples, but it is not limited to these examples.

Example: Preparation of Asiasari Radix Extracts

Asiasari Radix (250 g) was cut into small pieces and extracted with 70% methanol (750 ml) by the use of Soxhlet apparatus for 3 hours three times. Following filtration, the resulting methanol extract was concentrated by rotary evaporator and dried by freeze-dryer (Fr. 1). For fractionation with other organic solvents, 10 g of Fr. 1 was resuspended with 200 ml MeOH—$H_2O$ (4:1), which was then adjusted to pH 3 with 2M $H_2SO_4$. Then, it was extracted with equal volume of $CHCl_3$ three times and concentrated using a rotary evaporator, followed by freeze-dried (Fr. 2).

The water-soluble and $CHCl_3$ insoluble fraction was adjusted to pH 10 with $NH_4OH$ and subjected to extraction with equal volume of $CHCl_3$—MeOH (3:1) two times. The $CHCl_3$—MeOH (3:1) soluble fraction was concentrated and freeze dried (Fr. 3). The water-soluble and $CHCl_3$—MeOH (3:1) insoluble fraction was mixed with equal volume of MeOH and subjected to extraction three times. The MeOH soluble fraction was concentrated and freeze-dried (Fr. 4). The MeOH insoluble fraction was concentrated and freeze-dried (Fr. 5).

Experiment 1. Grease-Gap Recording Assay

1) Experimental Methods

Cortical wedges from rats were prepared, placed in two-compartment brain bath and experiments were performed as described by Harrison and Simmonds (British J. Pharmacol. 84, 381–391, 1985). 'Wedges' of rat cerebral cortex were prepared from the brains of male Wistar rats (200 g). The animal is decapitated and the brain rapidly removed into chilled oxygenated (95% $O_2$/5% $CO_2$) artificial cerebrospinal fluid (ACSF) containing (mM): NaCl 122, NaHCO3 25, KCl 3.1, $KH_2PO_4$ 0.4, $CaCl_2$ 1.3, $MgSO_4$ 1.4, D-glucose 10, (pH 7.4). 500–600 m coronal slices were taken and they were then placed in room temperature oxygenated ACSF and hemisected with a razor blade. A wedge of tissue was formed such that the dorsal cortical surface containing cerebral cortex and corpus callosum was approximately 1.5 mm wide and ventral surface was approximately 1 mm wide. The wedges were further incubated in ACSF for 2 hrs at room temperature.

Cortical wedges were placed in a two-compartment bath and a greased (high vacuum silicon grease) barrier placed such that a high-resistance seal was formed between the two compartments. Oxygenated ACSF was perfused through the two compartments separately at 2 ml/min for at least 1 hr. Asiasari Radix (AR) extracts of 10 μg/ml (fractions 1, 2, 3 or 4) were perfused 10 min before the application of AMPA (40 μM) for 2 min: AR extracts and AMPA were applied to the cortical compartment. The DC potential between the two compartments was monitored via Ag/AgCl electrodes. The signal was amplified and analyzed with the aid of McLab software.

2) Experimental Results

Depolarization of neuronal cells by AMPA is regarded as an index of stimulation by damages of neuronal cells. AMPA treatment (40 uM) for 2 min caused an increase in depolarization up to 0.79 mV. When AR extract (fraction 1) (10 ug/ml) was preincubated for 10 min and followed by AMPA treatment for 2 min, AMPA-induced increase in the depolarization was significantly decreased (FIG. 1A). The average inhibitory effect by the fraction 1 of AR extract was about 54% as compared to the control (FIG. 1B). These results suggest that AR extract (fraction 1) has significant neuroprotective actions against AMPA-induced neuronal damages.

Figure 2:
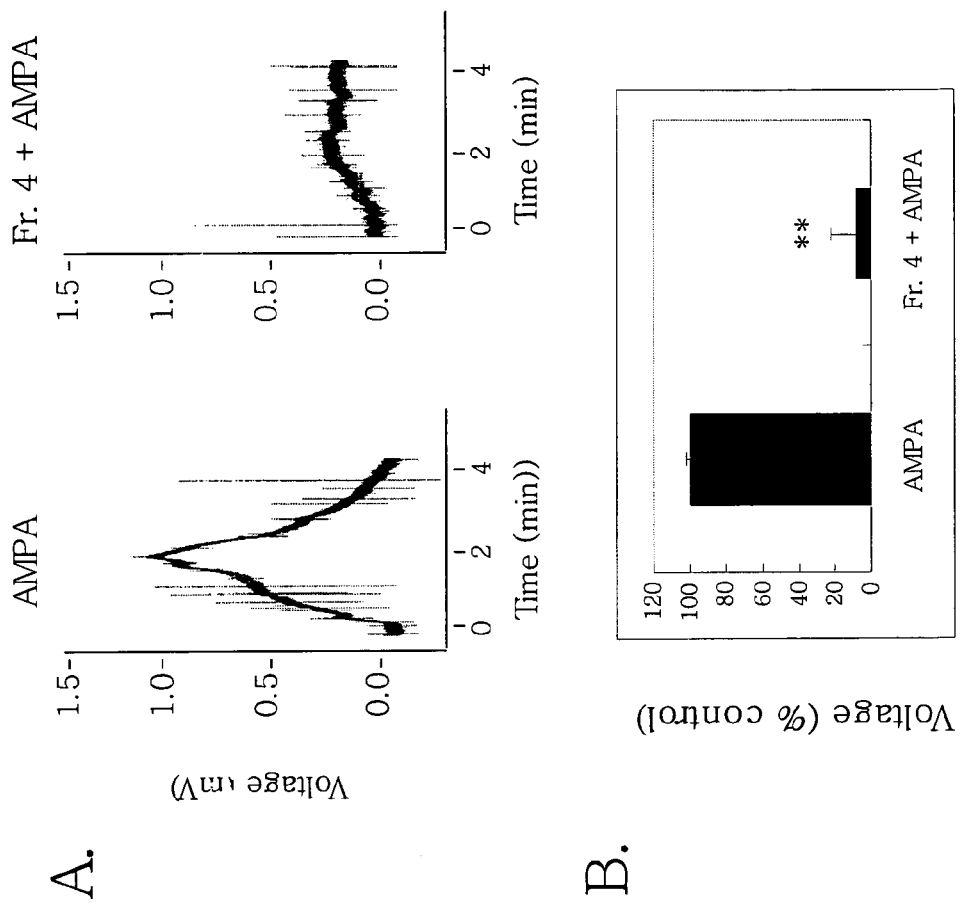
FIG. 2 shows fraction 4 of AR extract blocking the depolarization induced by AMPA in the rat cortical slices. Data are expressed as mean SD (n=5). **: p 0.01 with respect to the control.

Among the fractions from methanol extract of Asiasari Radix, fraction 4 has dramatic inhibitory action against AMPA-induced depolarization: it was about 92% protection against AMPA-induced neuronal damages (FIG. 2). On the other hand, fractions 2 and 3 were ineffective in the inhibition against AMPA-induced depolarization (data not shown).

Since the fraction 4 contains components which are insoluble in chloroform as well as in chloroform:methanol, it is devoid of terpenoids, phenolic compounds and sesamin which are soluble in organic solvents such as chloroform. Thus, it is suggested that the neuroprotective effects of fraction 4 be brought about by components other than sesamin, terpenoid and phenolic compounds etc.

Experiment 2. Cell Viability Assay (MTT Assay)

1) Experimental Methods

MTT assay is a method to measure mitochondrial redox with calorimeter and it is primarily used to know mitochondrial redox potential or cell viability (Mosmann T., J Immunol. Methods, 1983). PC 12 cells and C6 glial cells were grown in DMEM media with 10% fetal calf serum in 5% humidified $CO_2$ atmosphere at 37° C. PC12 cells were induced to differentiation into neuronal cells by the addition of nerve growth factor (100 ng/ml). Fresh NGF was added every 48 h and experiments were conducted after NGF treatment for 7 days.

The cells were plated in 96 well plates at a density of $1\times10^5$ cells/well. Cells were preincubated with AMPA (40 μM) and followed by the addition of AR fractions (10 μg/ml) for 24 hrs. MTT reagent (Sigma, USA) (5 mg/ml) was made in PBS (phosphate buffered saline) and filtered. The cells were then treated with MTT (final concentration, 0.5 mg/ml) and allowed to incubate for 3 hrs at 37° C. Cells containing active mitochondria form dark blue formazan by disintegrating tetrazolium ring. The culture media were removed and the cells were subjected to lysis in the presence of 100 Fl of DMSO and 10 Fl of Sorensen glycine buffer (0.1M glycine, 0.1M NaCl, pH 10.5). The absorbance was measured with spectrophotometer at 570 nm. The ratio of absorbance of experimental groups to control groups is expressed as % cell viability.

2) Experimental Results

Figure 3:
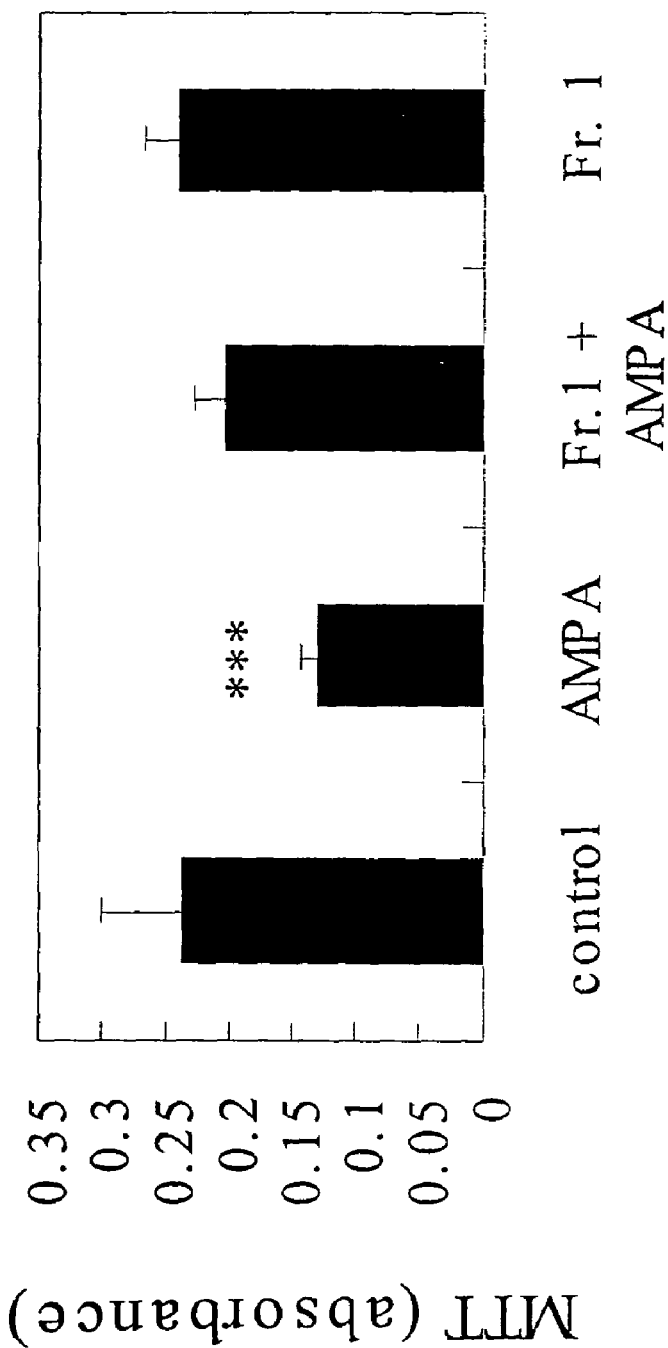
FIG. 3 shows fraction 1 of AR extract having inhibitory actions against neuronal cell damages induced by AMPA in the differentiated PC12 cells. Data are expressed as mean SD (n=5). ***: p 0.001 with respect to the control.
Figure 4:
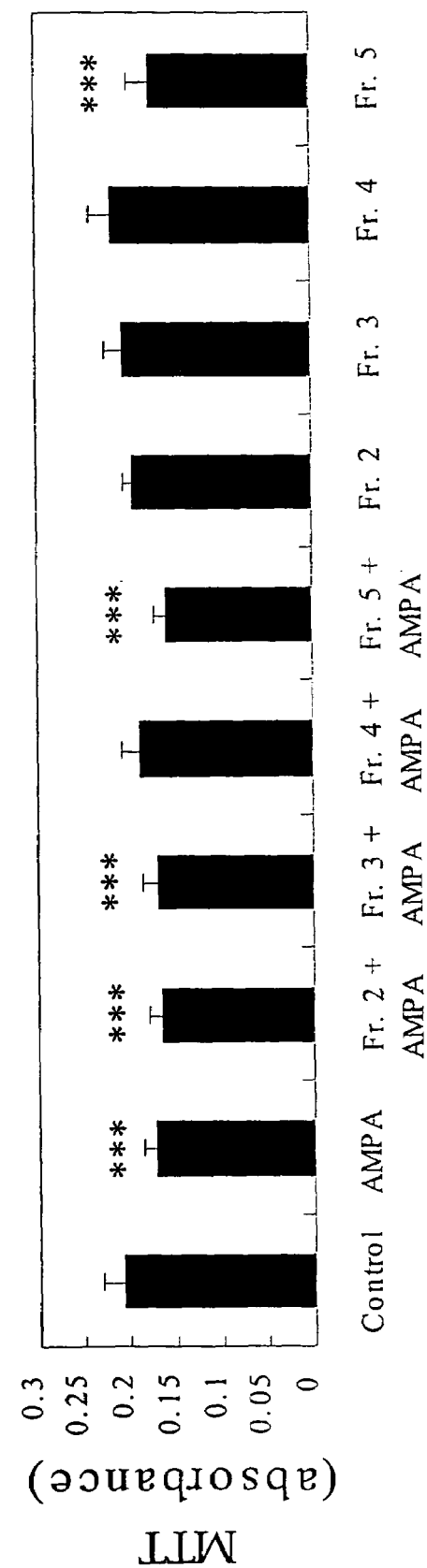
FIG. 4 shows the effects of fractions 2, 3, 4 and 5 of AR extract on neuronal cell damages induced by AMPA in the differentiated PC12 cells. Data are expressed as mean SD (n=5). ***: p 0.001 with respect to the control.
Figure 5:
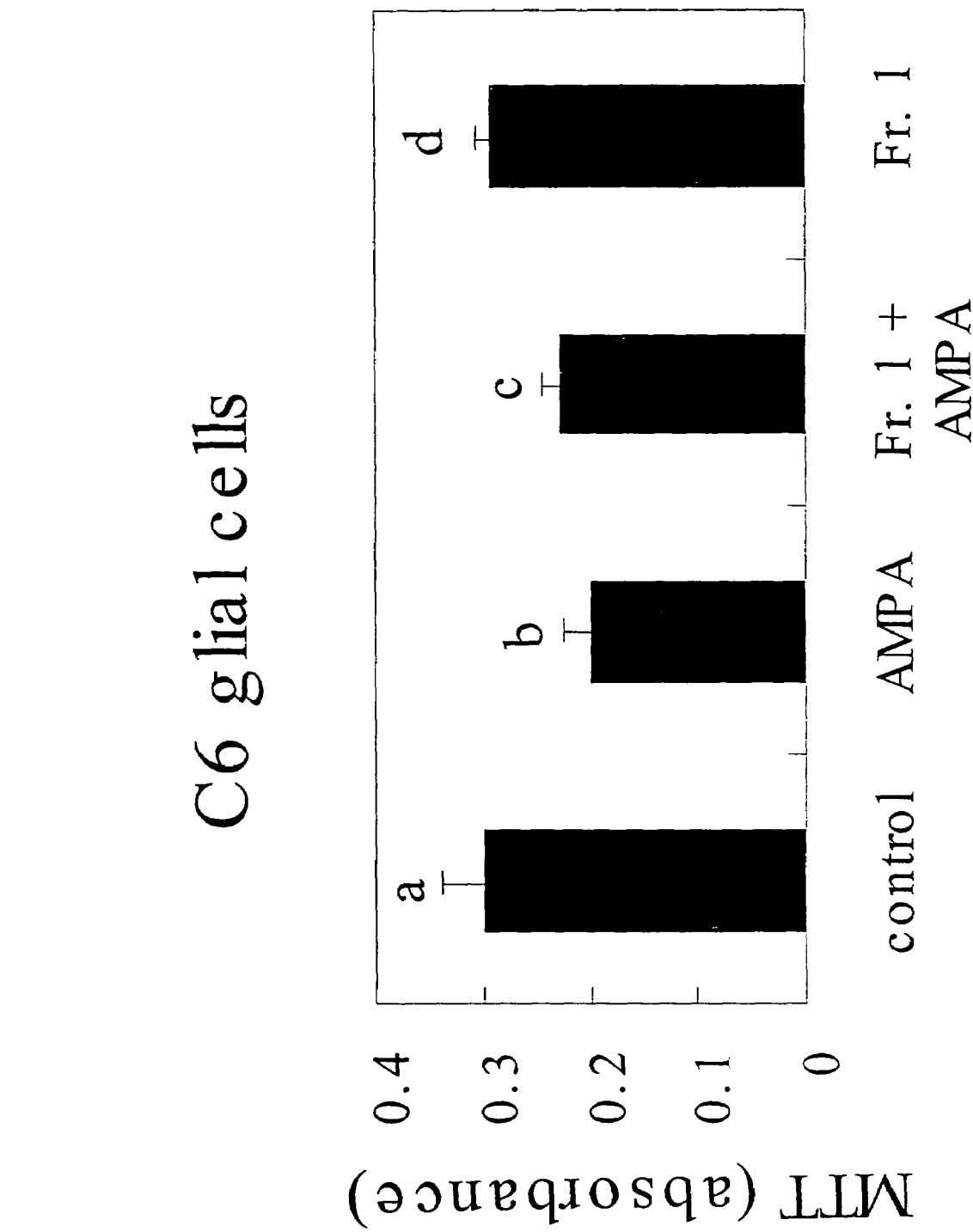
FIG. 5 shows fraction 1 of AR extract having inhibitory actions against cell damages induced by AMPA in the C6 glial cells. Data are expressed as mean SD (n=5). Bars not sharing a common letter are different at p 0.05 by Duncan's multiple range test.
Figure 6:
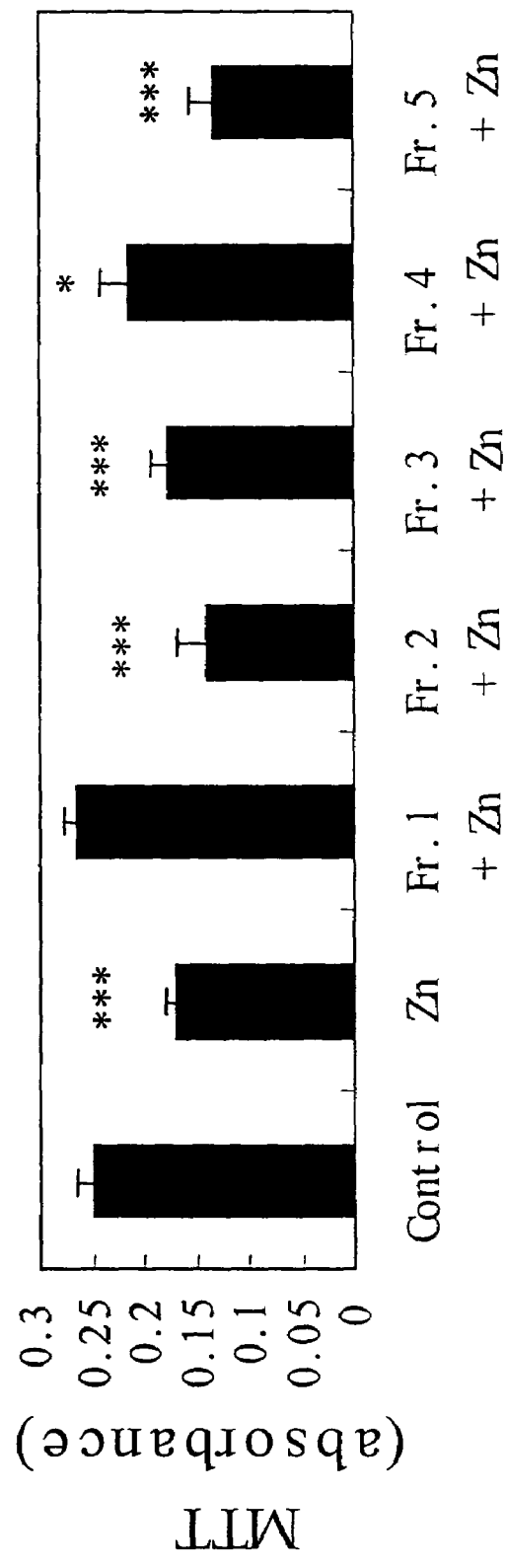
FIG. 6 shows fractions 1, 2, 3, 4 and 5 of AR extract having inhibitory actions against glial cell damages induced by $ZnCl_2$ in the C6 glial cells. Data are expressed as mean SD (n=5). *: p 0.05, ***: p 0.001 with respect to the control.

In the differentiated neuronal PC12 cells, AMPA (40 uM) caused approximately 50% reduction in the cell viability as compared to control whereas AR extract (fraction 1; 10 ug/ml) pretreatment caused more than 90% recovery from the reduction of cell viability caused by AMPA (FIG. 3). When fractions 2, 3, 4 or 5 were tested for their protective actions on cell viability, fraction 4 protected the AMPA-induced neuronal damages in the differentiated PC12 cells almost to the control level, suggesting it has active principles responsible for neuroprotection (FIG. 4). In C6 glial cells, AMPA caused approximately 35% reduction in the cell viability as compared to control whereas AR extract (fraction 1) pretreatment caused approximately 10% recovery from the reduction of cell viability caused by AMPA (FIG. 5). Since the original AR extract has relatively weaker protective effects against glial cell damages induced by AMPA, we tried to induce oxidative damages in the C6 glial cells with $ZnCl_2$ (100 uM) (FIG. 6). When fractions 1, 2, 3, 4 or 5 were pretreated, fraction 1 blocked the glial cell damages by 100% induced by Zn and fraction 4 inhibited the damages by 58% as compared to control.

Experiment 3. Memory Assay

1. NaNO2 Assay

It has been suggested that there is close relationship between deficit of oxidative metabolism in the brain by NaNO2 and cholinergic neurotransmission related to learning and memory. Therefore, the prolongation of survival time is regarded as an index of memory enhancement [Schindler et al., Drug Develop. Res. 4: 567–576, 1984].

1) Experimental Methods

Asiasari radix extract (fraction 1; 100 mg/Kg, I. P.) were administered to male mouse. After 60 min, $NaNO_2$ (250 mg/Kg, S. C.) was injected and cessation of respiration was recorded. The memory enhancing effects were analyzed by measuring and comparing the prolongation of survival times of control and treated groups.

The subfractions (fraction 2, 3, 4, and 5) of fraction 1 were also administered to male mouse (100 mg/kg, i.p.) and tested for the $NaNO_2$ memory assay as described above.

2) Experimental Results

Figure 7:
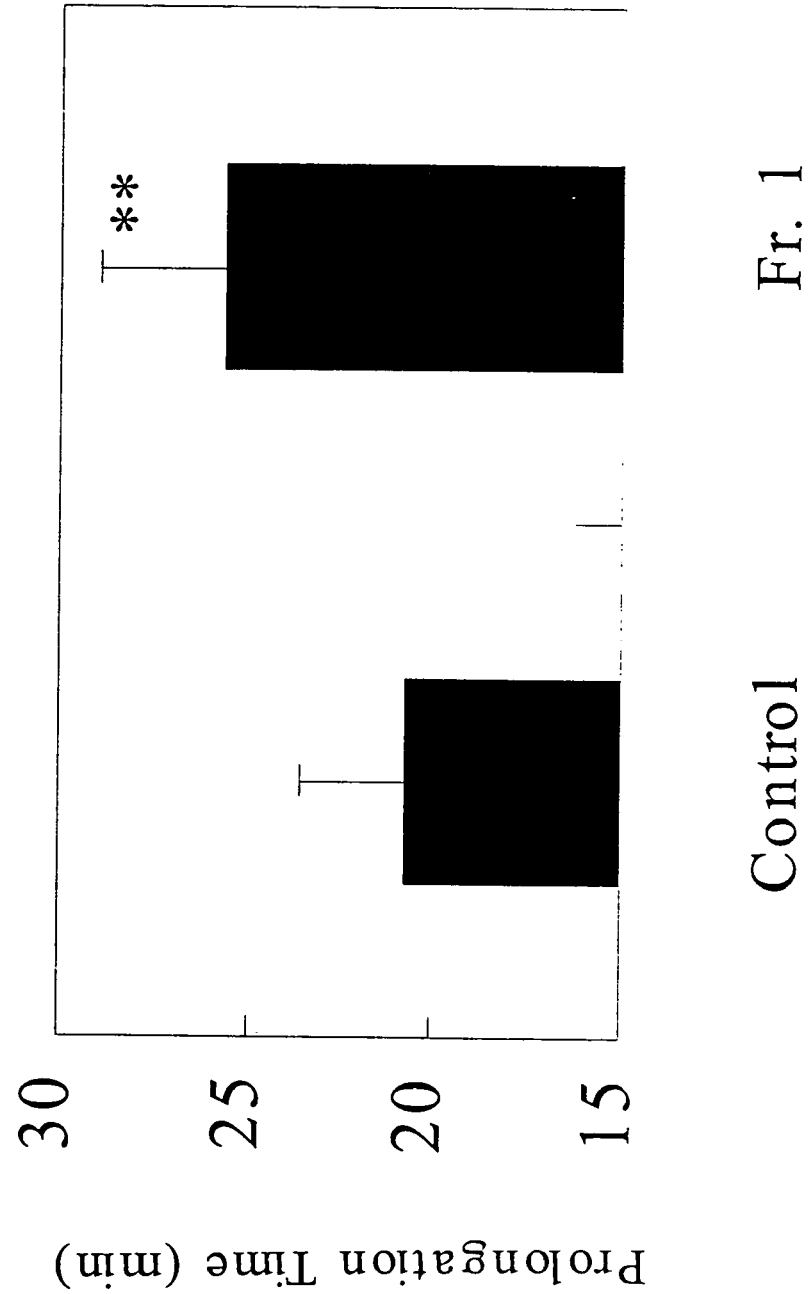
FIG. 7 shows fraction 1 of AR extract having increased memory in the $NaNO_2$ assay. Data are expressed as mean SD (n=8). **: p 0.01 with respect to the control.
Figure 8:
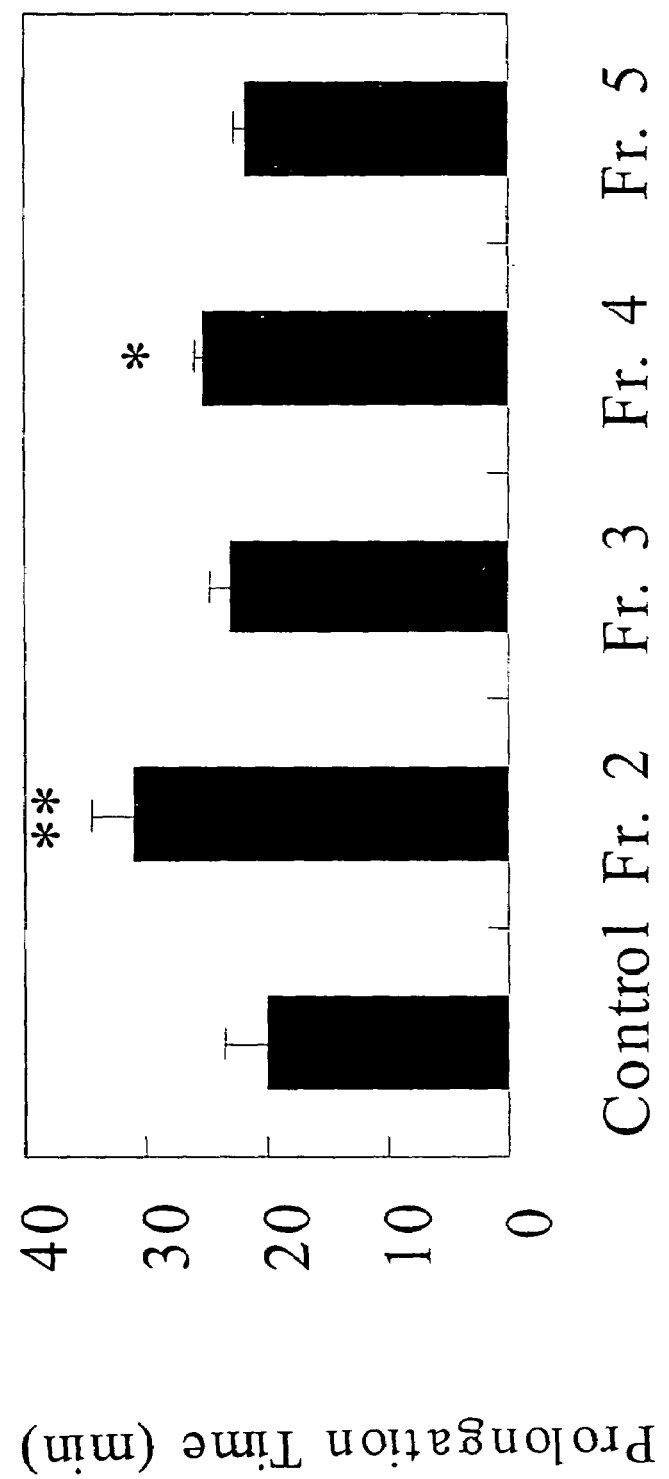
FIG. 8 shows the effects of fractions 2, 3, 4 and 5 of AR extract on the memory in the $NaNO_2$ assay. Data are expressed as mean SD (n=8). *: p 0.05, **: p 0.01 with respect to the control.
Figure 9:
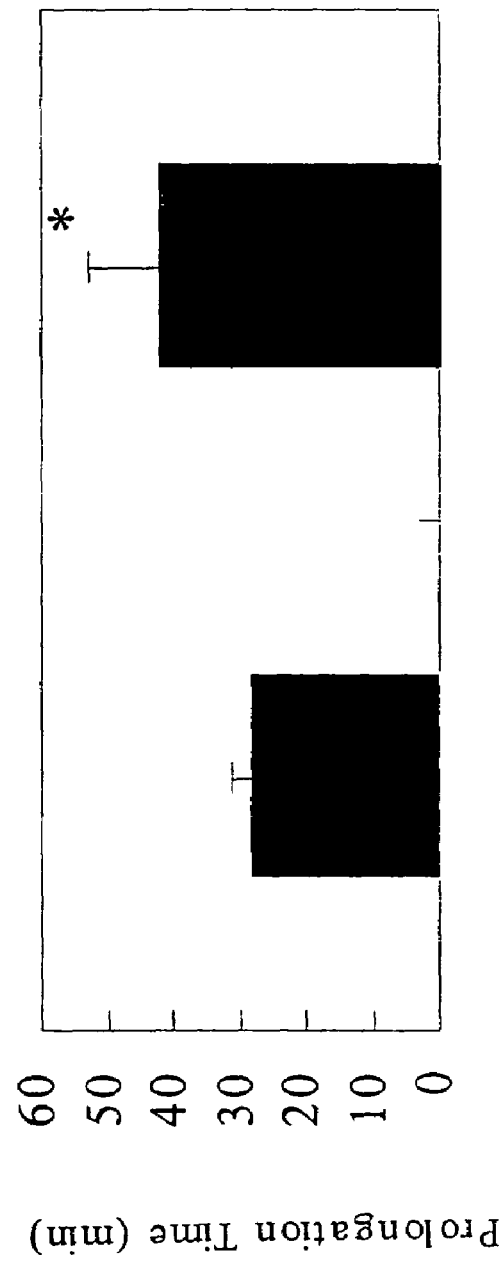
FIG. 9 shows administration of fraction 2 of AR extract via P.O. causing a significant increase of memory in the $NaNO_2$ assay. Data are expressed as mean SD (n=8). *: p 0.05 with respect to the control.

The original methanol extract of Asiasari Radix (fraction 1) administration (100 mg/Kg, I. P.) caused a 25% increase in the survival time as compared to control, indicating that it improves memory (FIG. 7). When fractions 2, 3, 4 and 5 were tested, fraction 4 caused about 25% increase in the survival time whereas fraction 2 caused the strongest memory enhancing effects (50% increase) among the fractions tested (FIG. 8). Subsequently, the fraction 2 was further tested as to whether oral administration could cause similar effects as i.p. administration. Fraction 2 was administered orally (10 mg/Kg) and after 60 min NaNO2 was administered. Administration of fraction 2 (10 mg/Kg, P. O.) caused approximately 50% increase in the memory (FIG. 9).

2. 8 Arm Radial Maze Test

To further improve that the fractions 1, 2 and 4 have memory enhancing activity, the 8 arm radial arm maze test was carried out as described by Ikonen and Riekkinen [European J Pharmacol. 382, 151–156, 1999].

1) Experimental Methods

Central part of the 8 arm radial maze measured 20 cm in diameter. Its arms are 25 cm long, 15 cm height, 6 cm wide. Briefly, two days of pre-training (5 min per day) allowed the mice to explore the baited radial arm maze. During the experimental phase, four of the arms were baited in a semi-random manner, with a unique combination of baited arms for each mouse. After each return to the center from an arm, the doors were closed for 5 s. The training was continued until all the baits were consumed or 15 min had passed. The test involved two parameters of memory function: 1) reference memory error, entry into unbaited arms; 2) working memory error, repeated entry into arms that had been visited within a trial [Gamoh et al.,. Clinical and experimental Pharmacology and Physiology 28, 266–270, 2001]. The fractions 1, 2 and 4 (10 mg/Kg/day, P.O.) was administered once a day for five days and tested for the 8 arm radial maze.

2) Experimental Results

Figure 10:
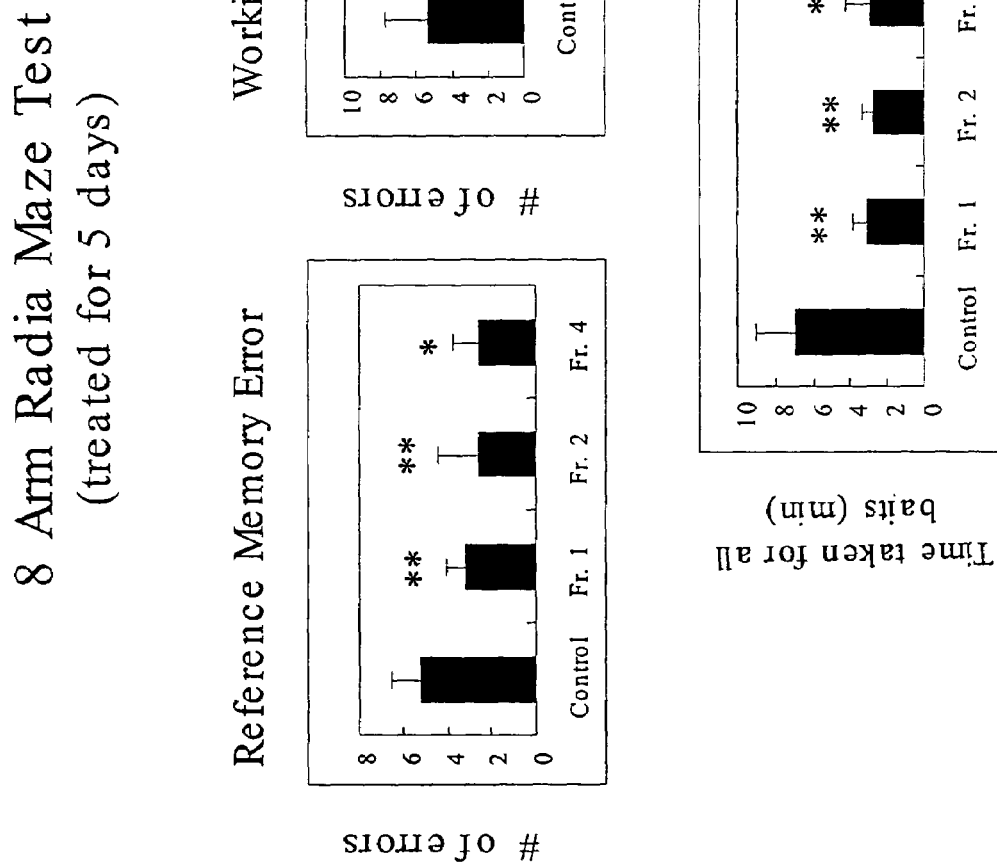
FIG. 10 shows the fractions 1, 2 and 4 of AR extract stimulating memory enhancement in the 8 radial arm maze assay. Data are expressed as mean SD (n=10). *: p 0.05, **: p 0.01 with respect to the control.

The reference memory error was reduced by 38%, 50% and 50% as compared to the control in response to fractions 1, 2 and 4, respectively while working memory error was reduced by 48%, 63% and 74% as compared to the control in response to fractions 1, 2 and 4, respectively (FIG. 10). The time taken to acquire all baits was reduced by 55%, 61% and 58% as compared to control in response to fractions 1, 2 and 4, respectively.

3. Passive Avoidance Test

1) Experimental Methods

The test was basically performed according to the step-through method described by Jarvik and Kopp [Jarvik, M. E. and Kopp, R. An improved one-trial passive avoidance learning situation. Pschol. Rep. 21, 221–224, 1967]. The Gemini Avoidance System (SD Instruments) was used for this experiments. The apparatus consists of a two-compartment acrylic box with a lightened compartment connected to a darkened one by an automatic guillotine door. Fractions 1, 2 or 4 (10 mg/kg/day, P.O.) was administered to mice once a day for three days and tested for the passive avoidance test. Mice were placed in the lighted box for 300 sec. Then, the guillotine door was open. Mice, as soon as they entered the dark compartment, received a punishing electrical shock (0.3 mA, 1 sec). The latency times for entering the dark compartment were measured in the training test and after 24 hr in the retention test. The maximum entry latency allowed in the retention session was 500 sec.

3) Experimental Results

Figure 11:
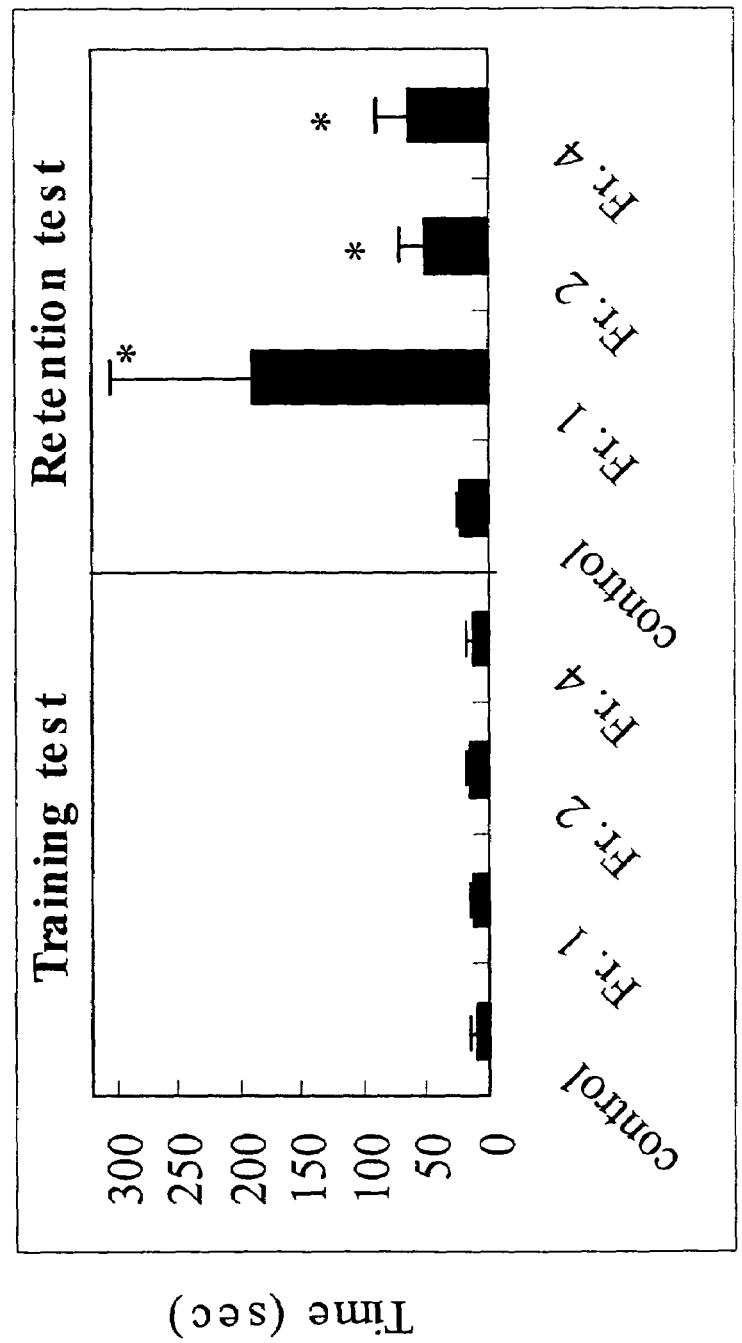
FIG. 11 shows fractions 1, 2 and 4 of AR extract stimulating memory enhancement in the passive avoidance test. Data are expressed as mean SD (n=10). *: p 0.05 with respect to the control.

There were no significant difference among the fractions of AR extract in the training session. In the retention session, however, fraction 1, fraction 2 or fraction 4 administration caused an increase in the step-through time by 8.1-fold, 2.2-fold and 2.7-fold, respectively as compared to the control (FIG. 11).

Experiment 4. Tyrosine Phosphorylation of Hippocampal Proteins

1) Experimental Methods

1. Preparation of Hippocampal Lysate

Male Sprague Dawley rats were decapitated 60 minutes after the administration of AR extracts 10 mg/kg and subjected to the isolation of hippocampus on 4° C. Hippocampal homogenates were prepared as described earlier with some modifications [Zhao, W., Chen, H., Xu, H., Moore, E., Meiri, N., Quon, M. J., Alkon, D. L., Insulin receptors and spatial memory. J. Biol. Chem. 274, 34893–34902, 1999]. The isolated hippocampus was resuspended with buffer A containing 50 mM Tris HCl, pH 7.4, 1 mM EDTA, 1 mM EGTA, 150 mM NaCl, 1% Triton X-100, 0.5 mM PMSF, 1 mM $Na_3VO_4$, 1 ug/ml of leupeptin and aprotinin and subjected to homogenization with a Potter-Elvehjem homogenizer. The lysates were then spun at 10,000×g for 20 min and the supernatant were subjected to protein assay and saved at 70 EC.

2. Immunoprecipitaion

Immunoprecipitation was performed as described earlier [Kim S. J., Kahn, C. R. Insulin stimulates phosphorylation of c-Jun, c-Fos and Fos-related proteins in cultured adipocytes. J. Biol. Chem. 269, 11887–11892, 1994]

Equal amount of proteins from hippocampal lysates were allowed to incubate with insulin receptor antibody for 1 hr at 4° C., followed by the addition of Protein A-Sepharose, and the immune complex was precipitated by centrifugation. The pellets were washed successively with 1 ml of buffer A (0.01M Tris, pH 7.4, 1M NaCl, 1% Nonidet P-40), buffer B (0.01M Tris, pH 7.4, 0.1M NaCl, 0.01M EDTA, 1% Nonidet P-40, 0.3% SDS) and buffer C (0.01M Tris, pH 7.4 and 1% Nonidet P-40). The final pellets were solubilized with Laemmli buffer containing 100 mM dithiothreitol, boiled for 5 min, centrifuged in a microcentrifuge, and the supernatant was subjected to SDS-PAGE and Western blot analysis with anti-pTyr antibody.

3. Western Blot Analysis

Equal amount of hippocampal proteins were applied to SDS polyacrylamide gel. Electrotransfer of proteins from the gels to nitrocelluose paper (Schleicher & Schuell) was carried out for 1 hr at 100 V (constant) as described by Towbin et al. [Towbin H., Staehelin, J., Gordon, J. Electric transfer of proteins from polyacrylamide gels to nitrocellulose sheets: procedure and some applications. Proc. Natl. Acad. Aci. USA 76, 4350–4354, 1979]. The filter papers were preincubated for 1 hr at 23° C. with PBS containing 0.1% Tween 20 and 3% bovine serum albumin and washed with PBS containing 0.1% Tween 20 three times for 10 min each. The blots were probed with pTyr or PERK antibodies for 1 hr at 23° C. The blots were then incubated with HRP-conjugated anti-rabbit IgG for 30 min and washed with PBS containing Tween 20 five times for 10 min each. The detection of immobilized specific antigens was carried out by ECL (NEN).

3) Experimental Results

Figure 12:
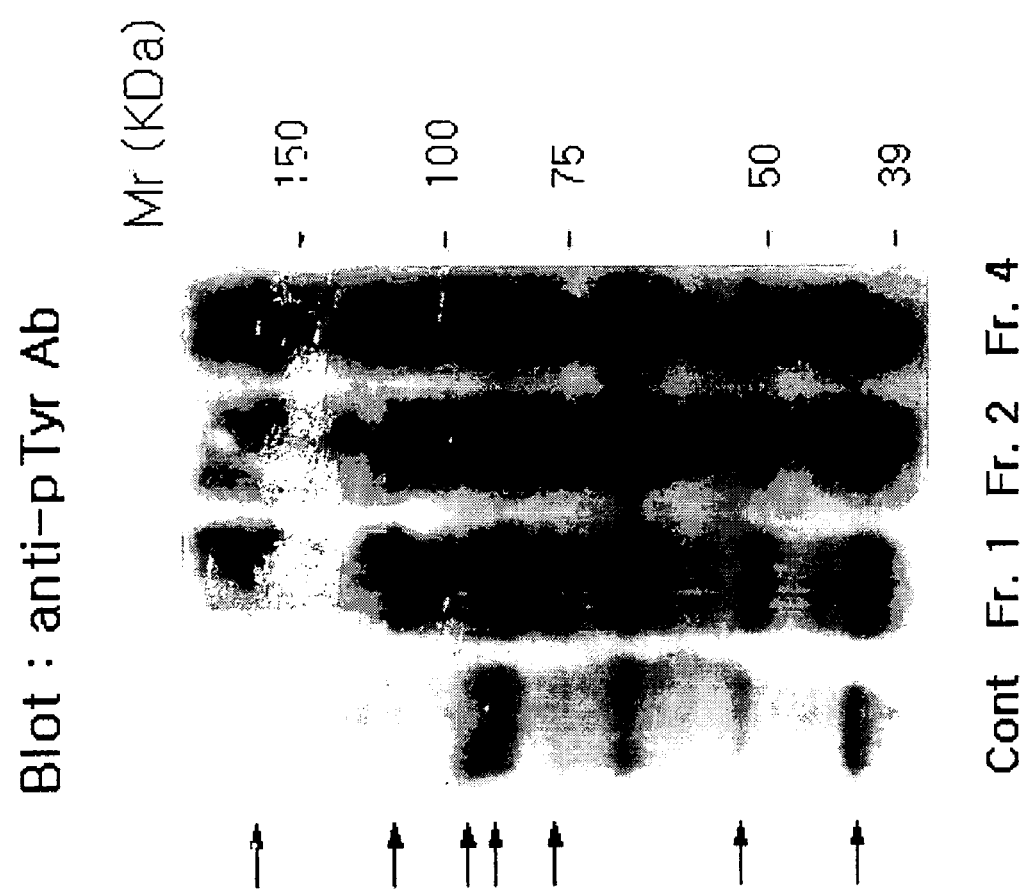
FIG. 12 shows fractions 1, 2 and 4 of AR extract stimulating tyrosine phosphorylation of rat hippocampal proteins.
Figure 13:
FIG. 13 shows tyrosine phosphorylation of insulin receptors by fractions 1, 2 and 4 of AR extract in rat hippocampus.
Figure 13:
Figure 14:
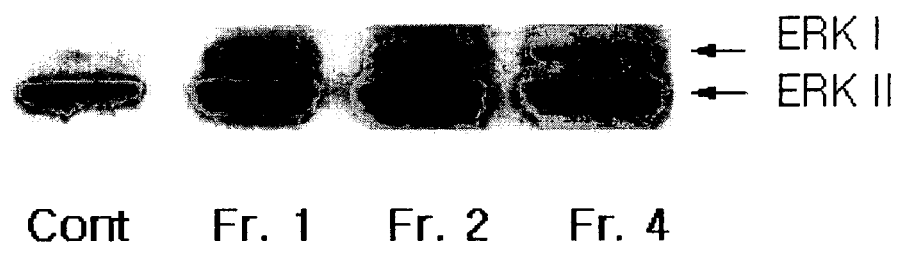
FIG. 14 shows fractions 1, 2 and 4 of AR extract activating ERK I and ERK II in rat hippocampus.

Since it has been suggested that tyrosine phosphorylation of the insulin receptors in hippocampus plays an important role in spatial memory, we have tested whether AR extracts have any effect on the tyrosine phosphorylation of hippocampal proteins. Tyrosine phosphorylation of a number of proteins with molecular sizes of ~180 kDa, 130 kDa, 95 kDa, 55 kDa and 42 kDa (FIG. 12). We further tested whether insulin receptor was tyrosine phosphorylated by the AR extracts. Insulin receptor phosphorylation was not detected under the basal condition whereas it was significantly stimulated by fraction 1 and fraction 2. The effect of fraction 1 was higher that that of fraction 2 (FIG. 13). In addition, the fraction 1, 2 and 4 of AR extracts have significantly stimulated ERK1 (44 kDa) and ERK2 (42 kDa) (FIG. 14). These results suggest that the fractions play an important role in memory and learning enhancement since activation of insulin receptor, ERK I and II are essential in memory and learning.

Experiment 5. Ex Vivo Cholinesterase Assay

1) Experimental Methods

Male SD rats were dosed p.o. with vehicle or fractions of AR extract (10 mg/kg). The rats were decapitated after 60 min, brains rapidly removed, hippocampus and corpora striata dissected free, weighed and homogenized as described above. Cholinesterase activity was measured as described by Ellman et al [Ellman, G. L., Courtney, K. D., Andres, V., Featherstone, R. M. A new and rapid colorimetric determination of acetylcholinesterase activity. Biochem. Pharmacol. 7, 88–95.1961]. Briefly, 3 ml of buffer I (100 mM phosphate, pH 8.0), 0.2 ml of 75 mM acetylthiocholine iodide and 0.1 ml of buffered Ellman's reagent (DTNB 10 mM, $NaHCO_3$ 15 mM) were mixed and allowed to incubate for 10 min at 25 EC. Then, 20 ml of enzyme sample was added and absorbance was measured at 30 sec intervals. The percent inhibition was calculated by comparison with the enzyme activity of the vehicle control group.

2) Experimental Results

Figure 15:
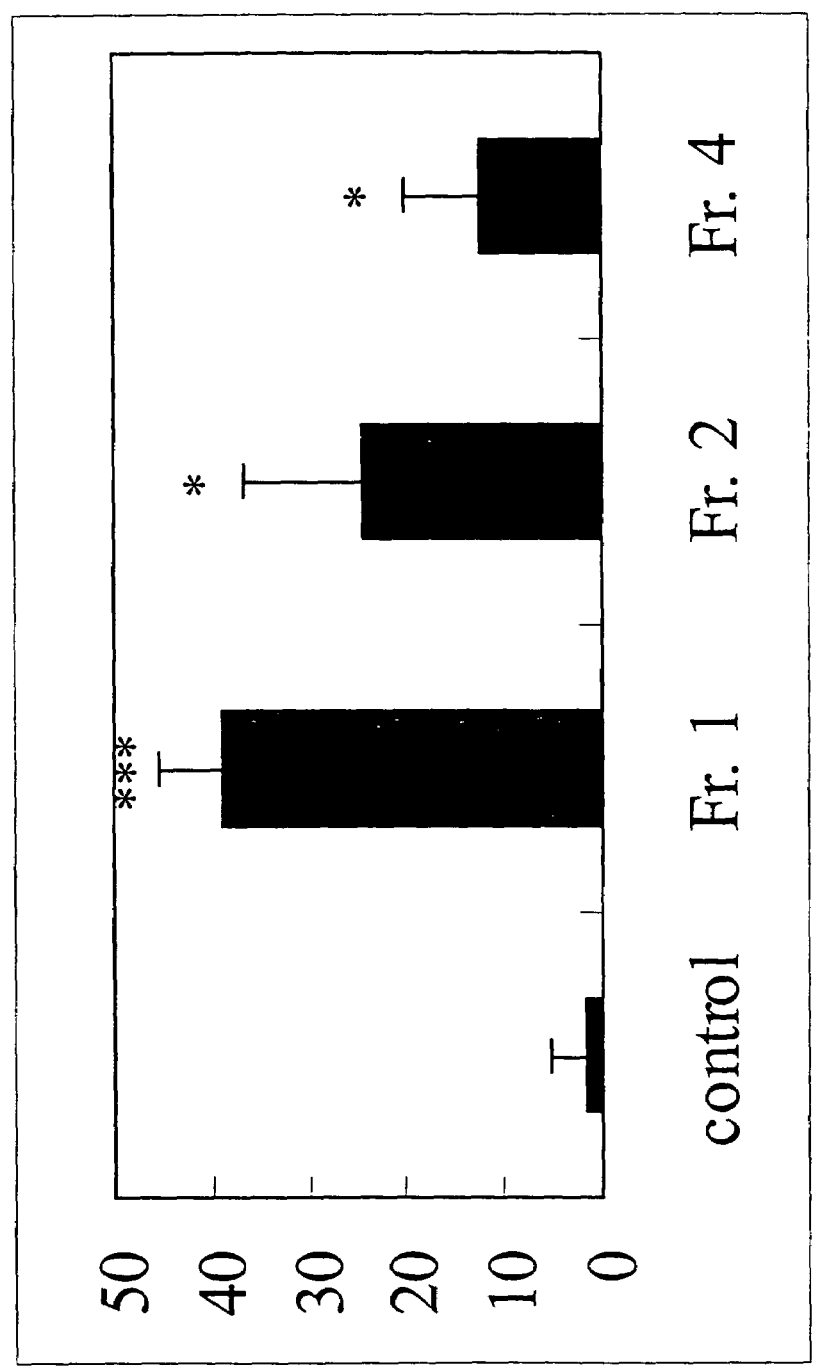
FIG. 15 shows fractions 1, 2 and 4 of AR extract inhibiting cholinesterase activity in rat hippocampus.

Considering that cholinesterase inhibition has been shown to improve cognitive functions, we tested whether AR extracts could have some inhibitory effects on hippocampal cholinesterase activity. Administration of fraction 1, 2 or 4 caused an inhibition of hippocampal cholinesterase activity by 39%, 24% or 12% as compared to control, respectively (FIG. 15).

Experiment 6. Oral Toxicity Test

1) Experimental Methods

ICR mouse (20 g) were housed for 1 week in a room with 50% relative humidity, 150–300 Lux, and controlled temperature (23 C) under 12 h light/dark cycle with free access to standard certified rodent diet and tap water. 25 mice were divided into 5 groups.

The Asiasari Radix extract (fraction 1) was dissolved in 0.1% Tween 80 and administered orally to 5 groups of the mice at the dose of 100 mg/Kg, 1,000 mg/Kg, 3,000 mg/Kg or 10,000 mg/Kg, respectively. For the next 7 days, changes of general symptoms and death were observed. At day 7, all mice were killed and internal organs were examined.

2) Experimental Results

Administration of the Asiasari radix extract did not cause any changes in general symptoms and the appearance of internal organs. LD50 of the fraction 1 of the Asiasari Radix appeared as 3,400 mg/Kg.

Preparation Example 1. Tablets

Tablets are formulated by conventional manufacturing methods according to the following compositions.

1-1. Tablets Composition

| | |
|---|---|
| Methanol extract of Asiasari Radix | 500.0 mg |
| Lactose | 500.0 mg |
| Talc | 5.0 mg |
| Magnesium stearate | 1.0 mg |

1-2. Tablets Composition
Chloroform fraction of methanol

| | |
|---|---|
| extract of Asiasari Radix | 50.0 mg |
| Lactose | 50.0 mg |
| Talc | 0.5 mg |
| Magnesium stearate | 0.1 mg |

1-3. Tablets Composition
Methanol Fraction of Methanol

| | |
|---|---|
| extract of Asiasari Radix | 50.0 mg |
| Lactose | 50.0 mg |
| Talc | 0.5 mg |
| Magnesium stearate | 0.1 mg |

Preparation Example 2. Capsules

Capsules were prepared by the following methods according to the composition described below. Asiasari Radix extracts were sifted out and mixed with excipients and filled up in gelatin capsules.

2-1. Capsules Composition

| | |
|---|---|
| Methanol extract of Asiasari Radix | 500.0 mg |
| Starch 1500 | 10.0 mg |
| Stearic acid magnesium BP | 100 mg |

2-2. Capsules Composition
Chloroform Fraction of Methanol

| | |
|---|---|
| extract of Asiasari Radix | 50.0 mg |
| Starch 1500 | 1.0 mg |
| Stearic acid magnesium BP | 10.0 mg |

2-3. Capsules Composition
Methanol Fraction of Methanol

| | |
|---|---|
| extract of Asiasari Radix | 50.0 mg |
| Starch 1500 | 1.0 mg |
| Stearic acid magnesium BP | 10.0 mg |

Preparation Example 3. Syrups

Syrups were formulated by the following methods according to the composition described below. First of all, sugars were dissolved in purified water and paraoxybenzoate, paraoxypropylbenzoate and Asiasari Radix extracts were added. The resulting mixtures were dissolved at 60C and allowed to cool down. Finally, purified water was added to make final volume of 150 ml.

3-1. Capsules Composition

| | |
|---|---|
| Methanol extract of Asiasari Radix | 5.0 g |
| Sugar | 95.1 g |
| Paraoxybenzoate | 80.0 mg |
| Paraoxypropylbenzoate | 16.0 mg |
| Purified water | to 150 ml |

3-2. Capsules Composition
Chloroform Fraction of Methanol

| | |
|---|---|
| extract of Asiasari Radix | 50.0 mg |
| Sugar | 95.1 g |
| Paraoxybenzoate | 80.0 mg |
| Paraoxypropylbenzoate | 16.0 mg |
| Purified water | to 150 ml |

3-3. Capsules Composition
Methanol Fraction of Methanol

| | |
|---|---|
| extract of Asiasari Radix | 50.0 mg |
| Sugar | 95.1 g |
| Paraoxybenzoate | 80.0 mg |
| Paraoxypropylbenzoate | 16.0 mg |
| Purified water | to 150 ml |

Preparation Example 4. Solutions

The following compositions are formulated by conventional methods for solutions and the solutions are filled up in brown bottles.

4-1. Solutions Composition

| | |
|---|---|
| Methanol extract of Asiasari Radix | 500.0 mg |
| Isoglucose | 20.0 g |
| Antioxidant | 5.0 mg |
| Methylparabenzoic acid | 2.0 mg |
| Distilled water | to 100.0 ml |

4-2. Solutions Composition
Chloroform Fraction of Methanol

| extract of Asiasari Radix | 500.0 mg |
|---|---|
| Isoglucose | 20.0 g |
| Antioxidant | 5.0 mg |
| Methylparabenzoic acid | 2.0 mg |
| Distilled water | to 100.0 ml |

4-3. Solutions Composition
Methanol Fraction of Methanol

| extract of Asiasari Radix | 500.0 mg |
|---|---|
| Isoglucose | 20.0 g |
| Antioxidant | 5.0 mg |
| Methylparabenzoic acid | 2.0 mg |
| Distilled water | to 100.0 ml |

Preparation Example 5. Powders

Powders were formulated as follows: the following components are mixed by conventional manufacturing methods for powders, filled into paper bags and completely sealed up.

5-1. Powders Composition

| Methanol extract of Asiasari Radix | 50.0 mg |
|---|---|
| Lactose | 100.0 mg |
| Talc | 5.0 mg |

5-2. Powders Composition
Chloroform Fraction of Methanol

| extract of Asiasari Radix | 50.0 mg |
|---|---|
| Lactose | 100.0 mg |
| Talc | 5.0 mg |

5-3. Powders Composition
Methanol Fraction of Methanol

| extract of Asiasari Radix | 50.0 mg |
|---|---|
| Lactose | 100.0 mg |
| Talc | 5.0 mg |

Preparation Example 6. Injections

Injections were formulated by the following conventional manufacturing methods for injections according to the composition described below. The prepared injections are filled up in ampules of 2.0 ml volume and sterilized.

6-1. Injections Composition

| Methanol extract of Asiasari Radix | 50.0 mg |
|---|---|
| Antioxidant | 1.0 mg |
| Tween 80 | 1.0 mg |
| Distilled water for injections | to 2.0 ml |

6-2. Injections Composition
Chloroform Fraction of Methanol

| extract of Asiasari Radix | 50.0 mg |
|---|---|
| Antioxidant | 1.0 mg |
| Tween 80 | 1.0 mg |
| Distilled water for injections | to 2.0 ml |

6-3. Injections Composition
Methanol Fraction of Methanol

| extract of Asiasari Radix | 50.0 mg |
|---|---|
| Antioxidant | 1.0 mg |
| Tween 80 | 1.0 mg |
| Distilled water for injections | to 2.0 ml |

Effectiveness of the Invention

The composition containing Asiasari Radix extracts bring about not only prevention and treatment of neurodegenerative diseases caused by brain cell damages but also induction effect of memory improvement. It could be usefully utilized for the moderns who are exposed to dangerous brain damages due to various environmental stresses as well as for those who have decreased memory activity including dementia.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A composition containing Asiasari Radix extracts subjected to a pH adjustment with an acid and then further subjected to an additional pH adjustment with a base thereafter for protecting brain cells from excitotoxicity and improving memory.

2. The composition of claim 1 wherein content of the Asiasari Radix extracts ranges from 0.5 to 50% by weight per total weight of the composition.

3. The composition of claim 1 wherein prior to the acid pH adjustment, the Asiasari Radix extracts are extracted with a lower alcohol containing between about 1 carbon atom and about 4 carbon atoms.

4. The composition of claim 3 wherein the lower alcohol is selected from the group consisting of methanol, ethanol, acetone, chloroform, methylenechloride, ether, ethylacetate, and combinations thereof.

5. The composition of claim 1 wherein the composition further comprises carriers, excipients and diluents.

6. The composition of claim 1 wherein the composition is formulated as oral preparations.

7. The composition of claim 6 wherein the oral preparations are powders, tablets, capsules, suspensions, syrups and aerosols.

8. The composition of claim 1 wherein the composition is formulated as external applications.

9. The composition of claim 1 wherein the composition is formulated as suppositories.

10. The composition of claim 1 wherein the composition is formulated as sterile injections.

11. A method for producing Asiasari Radix extracts, said method comprising the steps:

a) extracting Asiasari Radix with a solution comprising a lower alcohol having from 1–4 carbon atoms and an organic solvent, said organic solvent being selected from the group consisting of acetone, chloroform, methylenechloride, ether and ethylacetate, said step of extracting being conducted at a temperature from between 5 degrees Celsius to 80 degrees Celsius and for a duration extending from 15 minutes to 48 hours, said lower alcohol and said organic solvent being operative to solubilize a portion of said Asiasari Radix;

b) adjusting the pH of said solution of said lower alcohol and organic solvent such that said solution has a pH from between 2–4, said pH being adjusted with an acid;

c) contacting said solution with a base such that said pH is adjusted to between 9–12; and d) evaporating said solution comprising said lower alcohol and said organic solvent to isolate said portion of said Asiasari Radix solubilized in said lower alcohol and organic solvent.

12. The composition formed by the method of claim 11.

13. The method of claim 11 wherein when said solution is contacted with said base, said solution is further contacted with an equal volume of chloroform.

14. The composition produced by the method of claim 13.

* * * * *